(12) United States Patent
Perrey

(10) Patent No.: US 10,664,977 B2
(45) Date of Patent: May 26, 2020

(54) APPARATUS AND METHOD FOR IMAGE-BASED CONTROL OF IMAGING SYSTEM PARAMETERS

(71) Applicant: General Electric Company, Schenectady, NY (US)

(72) Inventor: Christian Fritz Perrey, Mondsee (AT)

(73) Assignee: General Electric Company, Schenectady, NY (US)

( * ) Notice: Subject to any disclaimer, the term of this patent is extended or adjusted under 35 U.S.C. 154(b) by 78 days.

(21) Appl. No.: 15/907,888

(22) Filed: Feb. 28, 2018

(65) Prior Publication Data

US 2019/0266732 A1  Aug. 29, 2019

(51) Int. Cl.
| | |
|---|---|
| *G06K 9/00* | (2006.01) |
| *G06T 7/20* | (2017.01) |
| *A61B 8/08* | (2006.01) |
| *G06T 7/00* | (2017.01) |
| *A61B 8/00* | (2006.01) |

(52) U.S. Cl.
CPC .............. *G06T 7/20* (2013.01); *A61B 8/4254* (2013.01); *A61B 8/5276* (2013.01); *A61B 8/54* (2013.01); *G06T 7/0002* (2013.01); *A61B 8/481* (2013.01); *G06T 2207/10132* (2013.01)

(58) Field of Classification Search
CPC ..... A61B 8/4254; A61B 8/481; A61B 8/5276; A61B 8/54; G06T 2207/10132; G06T 7/0002; G06T 7/20
See application file for complete search history.

(56) References Cited

U.S. PATENT DOCUMENTS

| | | | |
|---|---|---|---|
| 7,474,766 B2 | 1/2009 | Kornaki | |
| 7,705,884 B2 | 4/2010 | Pinto et al. | |
| 7,995,097 B2 | 8/2011 | Tzur et al. | |
| 8,010,180 B2 | 8/2011 | Quaid et al. | |
| 8,155,729 B1 | 4/2012 | Hsieh et al. | |
| 8,190,016 B2 | 5/2012 | Pozniansky et al. | |
| 8,718,338 B2 | 5/2014 | Soubelet et al. | |
| 2006/0058652 A1 | 3/2006 | Little | |
| 2007/0066880 A1 | 3/2007 | Lee et al. | |
| 2008/0291288 A1 | 11/2008 | Tzur et al. | |
| 2010/0049048 A1 | 2/2010 | Miyachi | |
| 2010/0099988 A1* | 4/2010 | Kurita ...................... | A61B 8/08 600/443 |
| 2011/0218436 A1 | 9/2011 | Dewey et al. | |
| 2012/0071758 A1* | 3/2012 | Lachaine ................ | A61B 8/085 600/439 |
| 2012/0323528 A1 | 12/2012 | Davis et al. | |
| 2014/0031688 A1 | 1/2014 | Perrey et al. | |

(Continued)

FOREIGN PATENT DOCUMENTS

EP  1097674 A2 *  5/2001  .............. A61B 8/06

*Primary Examiner* — Ian L Lemieux
(74) *Attorney, Agent, or Firm* — The Small Patent Law Group LLC; Dean D. Small

(57) ABSTRACT

An apparatus includes one or more processors configured to monitor motion of an imaging probe in an imaging system operating according to one or more parameters. The imaging probe is configured to output image data representative of an imaged body. The one or more processors are configured to change the one or more parameters of the imaging system based on the motion of the imaging probe that is monitored.

24 Claims, 4 Drawing Sheets

(56) References Cited

U.S. PATENT DOCUMENTS

| | | |
|---|---|---|
| 2014/0128739 A1* | 5/2014 | Sundaran ............. A61B 8/4254 600/459 |
| 2014/0187946 A1 | 7/2014 | Miller et al. |
| 2014/0243671 A1* | 8/2014 | Holl .................... A61B 8/4209 600/443 |
| 2016/0354060 A1 | 12/2016 | Perrey et al. |
| 2017/0238904 A1 | 8/2017 | Perrey et al. |
| 2018/0214134 A1* | 8/2018 | Kim ........................ A61B 8/54 |

* cited by examiner

APPARATUS AND METHOD FOR IMAGE-BASED CONTROL OF IMAGING SYSTEM PARAMETERS

FIELD

The subject matter disclosed herein relates generally to imaging systems.

BACKGROUND

Imaging systems generate image data representative of imaged bodies based on a variety of parameters of the imaging systems. These parameters dictate how the bodies are imaged, and may have fixed values or be manually changed by users of the imaging systems.

For example, some ultrasound imaging systems include software tools (e.g., applications) for automatically segmenting follicles in ultrasound volumes. These tools can have user-selectable sensitivity sliders that allow a user of an ultrasound system to manually change the sensitivity at which images are acquired. Low sensitivities selected by the user can result in the ultrasound imaging systems detecting fewer follicles in the ultrasound volumes. Higher sensitivities selected by the user can result in more follicles being detected, but this also can result in more false-positive automated detections of follicles by the imaging systems.

The users may then need to find the sensitivity (or other imaging parameter) that provides helpful image data for revealing or detecting bodies within the image (e.g., follicles), but that is not too sensitive (or have an otherwise extreme value) that results in falsely detecting bodies in the image(s) or incorrectly identifying bodies in the image(s). For manually selected imaging parameters, this can result in the user having to repeatedly select and/or change the value(s) of the imaging parameters.

This can be a difficult operation for some types of imaging systems. With respect to an ultrasound imaging system, the user usually has a hand-held ultrasound imaging probe that is held by the user toward a region of interest, while the user also concurrently reviews a display showing a representation of the image data and changes one or more imaging parameters. The user may not be able to maintain the desired region of interest within the field of view of the imaging probe while also changing the value of the imaging system parameter.

BRIEF DESCRIPTION

In one embodiment, an apparatus includes one or more processors configured to monitor motion of an imaging probe in an imaging system operating according to one or more parameters. The imaging probe is configured to output image data representative of an imaged body. The one or more processors are configured to change the one or more parameters of the imaging system based on the motion of the imaging probe that is monitored.

In one embodiment, a method includes obtaining image data of an imaged body using a moveable imaging probe of an imaging system that operates according to one or more parameters, monitoring motion of the imaging probe while the imaging probe is obtaining the image data of the imaged body, and changing the one or more parameters of the imaging system using one or more processors based on the motion of the imaging probe that is monitored.

In one embodiment, a tangible and non-transitory computer-readable storage medium is provided that includes instructions that direct one or more processors to monitor motion of an imaging probe of an imaging system that operates according to one or more parameters. The motion of the imaging probe is monitored while the imaging probe is obtaining the image data of an imaged body. The motion of the imaging probe is monitored based on one or more of data output by one or more sensors operatively coupled with the imaging probe or based on one or more changes in the image data. The instructions also direct the one or more processors to change the one or more parameters of the imaging system using one or more processors based on the one or more of the data output by the one or more sensors or based on the one or more changes in the image data.

BRIEF DESCRIPTION OF THE DRAWINGS

The inventive subject matter described herein will be better understood from reading the following description of non-limiting embodiments, with reference to the attached drawings, wherein below.

DETAILED DESCRIPTION

Figure 1:
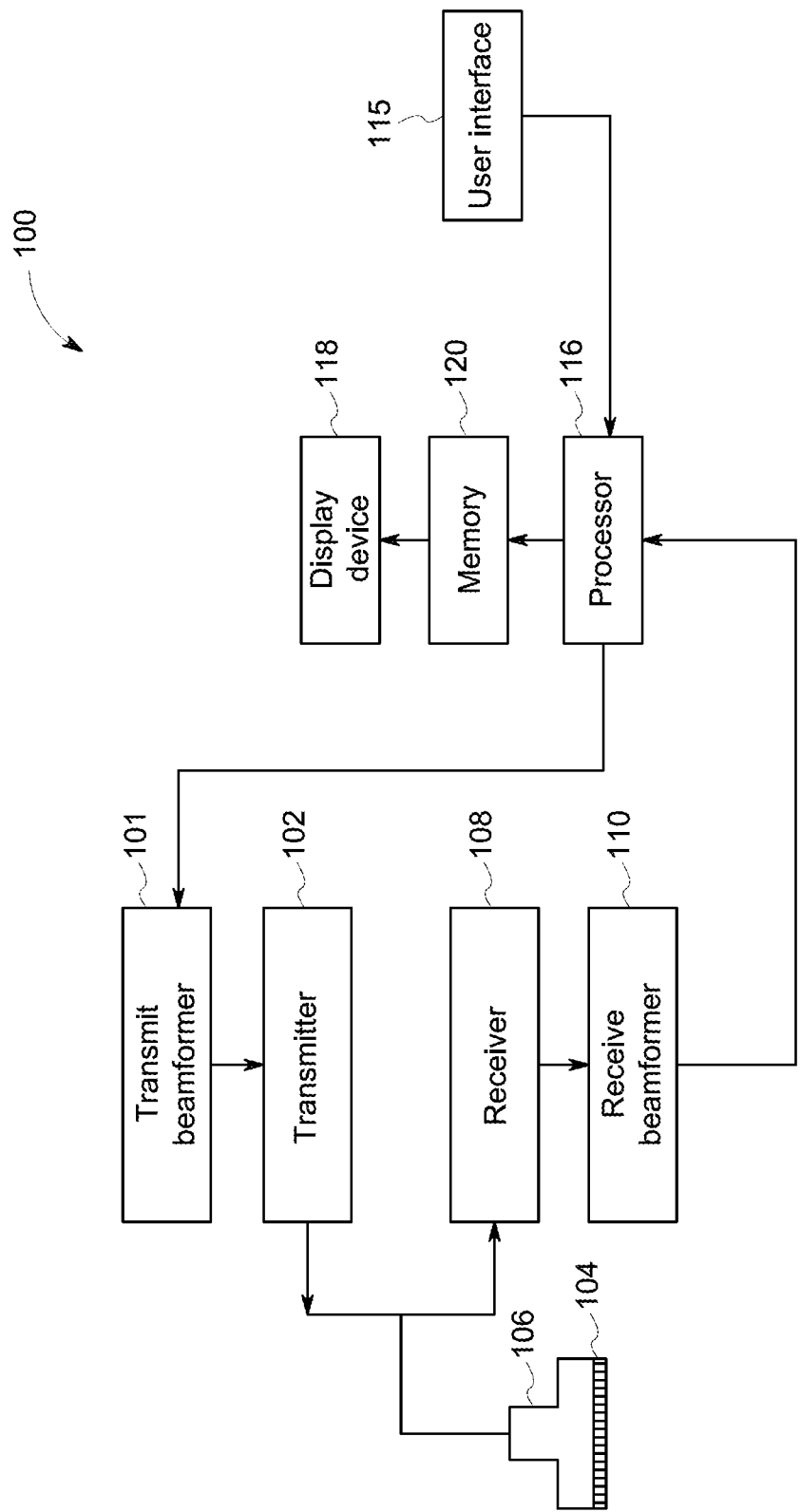
FIG. 1 is a schematic diagram of an ultrasound imaging system in accordance with an embodiment.

One or more embodiments of the inventive subject matter described herein provide for apparatuses and methods of imaging systems that monitor image quality and/or motion of an imaging probe and, based on the image quality and/or probe motion (or absence of probe motion), automatically change one or more parameters of the imaging systems. The parameters of the imaging system dictate how image data is obtained, processed, and/or visually presented. For example, the parameters of the imaging system can be settings of the imaging system, such as a sensitivity at which the region of interest is imaged, a gain at which information is sensed by the probe, a time gain compensation at which information is sensed by the probe, a line density, a receipt frequency, a speckle reduction filter setting, a render setting, a brightness, a focal point, or the like.

The motion that is monitored can be movement of the imaging probe or an absence of motion of the probe. For example, the apparatuses and methods can examine the imaging probe to determine whether the probe is moving, how rapidly the probe is moving, the direction(s) in which the probe is moving, how long the probe has been moving, whether the probe is being held stationary, how long the probe has been held stationary, or the like. Not all embodiments of the inventive subject matter described herein are limited to monitoring movement of the probe as the motion of the probe. Monitoring a stationary probe is included in monitoring motion of the probe in at least one embodiment of the inventive subject matter described herein. For example, monitoring the motion of the probe can involve determining whether the probe is being held stationary and is not moving relative to a body being imaged.

The probe of the imaging system can be the device that senses information about the region of interest or the imaged body. For example, the probe can be an ultrasound imaging probe that emits ultrasound pulses and detects echoes of the pulses. Optionally, the probe can be a camera, lens system of a camera, infrared emitter and/or detector, a photoemitter and/or detector (e.g., for LiDAR systems, structured light array systems, etc.), x-ray detector, etc.

The parameter of the imaging system can be changed by different amounts based on the type (e.g., category) of probe motion that is detected, the speed at which the probe is moved, how long the probe is held stationary, how long the probe is moving, etc. The parameter can be one of a variety of settings of the imaging system that changes or dictates how the region of interest of the imaging probe is imaged and/or how the image data is presented. For example, the parameter (and the values of the parameter that are changed or set based on the monitored motion of the imaging probe) can include a sensitivity at which the region of interest is imaged, a gain at which information is sensed by the probe, a time gain compensation at which information is sensed by the probe, a line density, a receipt frequency, a speckle reduction filter setting, a render setting, a brightness, a focal point, or the like.

The apparatus and method can automatically change one or more imaging parameters based on the motion of the probe that is monitored. This automatic changing of the parameter can occur without operator intervention. For example, the apparatus and method can change a value of the imaging system parameter without receipt of any other operator input related to or directing a change in the parameter. This solves the problem of the imaging system parameter being unable to be changed without the operator that is controlling the probe having to also manually change (via touch, speech, or the like) the parameter. The operator can focus on moving or holding the probe stationary while image data is generated by the probe, instead of the attention of the operator being divided between moving or holding the probe, examining the image data, and changing the value(s) of one or more imaging system parameters.

In one embodiment, the apparatus and method calculate an image quality measure based on the motion of the imaging probe that is monitored. This image quality measure can be a quantitative value indicative of the quality of the image data based on the motion of the probe. For example, a probe generating image data of a region of interest having many motion artifacts may have a lower image quality measure than when the probe generates image data of the same or other region of interest having fewer motion artifacts. The apparatus and method can calculate the quality measure based on the image data of the probe, and also change the value of one or more imaging system parameters based on the quality measure that is calculated.

As one example of the inventive subject matter used in conjunction with an ultrasound imaging system, a user can use an ultrasound probe to image a target organ in an imaged patient. The user can then hold the probe stationary, and the apparatus or method can change the parameter of the imaging system with respect to time the longer that the probe is held stationary. For example, the apparatus or method can use a counter to increase the sensitivity of the probe in direct proportion to how long the user holds the probe stationary. For example, the longer that the user holds the probe in place, the more the sensitivity parameter of the imaging system increases in value. User feedback can be generated and provided via a color bar or the like on a display of the imaging system to show the progress or current value of the sensitivity parameter. As another example, the segmentation result related to a specific sensitivity parameter could be shown to the user.

In another example, the apparatus and method can monitor probe motion to determine if and/or when movement of the probe stops. Responsive to this movement stopping, the imaging system can start a counter and increase the value of an imaging system parameter. Responsive to the movement beginning (from the probe being stationary), the value of the parameter can stop increasing and the current value of the parameter and/or image data can be shown to the user.

As another example, a user can move the imaging probe and review the image data representative of a region of interest. Once the region of interest is found, the user can slow movement of the probe so that a decrease in the monitored motion is detected. Responsive to detecting the decrease in movement, the apparatus and method can direct the imaging system to begin acquiring image data, such as by starting to record a two-dimensional cine or video. The user may later begin moving the probe to search for another target. This results in the movement of the probe increasing, and the change in probe motion is detected. Responsive to detecting the commencement of probe movement, the apparatus can direct the imaging system to stop recording the two-dimensional cine or video.

At least one technical effect of the inventive subject matter described herein provides for an imaging system that allows an operator to image a region of interest in an imaged body while concurrently modifying parameters of the imaging system that dictate how the image data is obtained and/or generated, without providing other intervention or action with the imaging system). This can reduce the operator-interface requirements of the imaging system so that the imaging system is able to change the parameters used to create the imaging system without requiring additional input aside from movement of the probe, but while imaging of the body continues or is being performed.

FIG. 1 is a schematic diagram of an ultrasound imaging system 100 in accordance with an embodiment. The ultrasound imaging system 100 includes a transmit beamformer 101 and a transmitter 102 that drive elements 104 within a probe 106 to emit pulsed ultrasonic signals into a body (not shown). According to an embodiment, the probe 106 may be a two-dimensional matrix array probe. However, any other type of probe capable of acquiring four-dimensional ultrasound data may be used according to other embodiments. The four-dimensional ultrasound data can include ultrasound data such as multiple three-dimensional volumes acquired over a period of time. The four-dimensional ultrasound data can include information showing how a three-dimensional volume changes over time.

The pulsed ultrasonic signals are back-scattered from structures in the body, such as blood cells or muscular tissue, to produce echoes that return to the elements 104. The echoes are converted into electrical signals, or ultrasound data, by the elements 104 and the electrical signals are received by a receiver 108. The electrical signals representing the received echoes are passed through a receive beamformer 110 that outputs ultrasound data. The probe 106 may contain electronic circuitry to do all or part of the transmit and/or the receive beamforming. For example, all or part of the transmit beamformer 101, the transmitter 102, the receiver 108 and the receive beamformer 110 may be situated within the probe 106. Scanning may include acquiring data through the process of transmitting and receiving ultrasonic signals. Data generated by the probe 106 can include one or more datasets acquired with an ultrasound imaging system. A user interface 115 may be used to control operation of the ultrasound imaging system 100, including, to control the input of patient data, to change a scanning or display parameter, and the like.

The ultrasound imaging system 100 also includes one or more processors 116 that control the transmit beamformer 101, the transmitter 102, the receiver 108 and the receive beamformer 110. The processors 116 are in electronic communication with the probe 106 via one or more wired and/or wireless connections. The processors 116 may control the probe 106 to acquire data. The processors 116 control which of the elements 104 are active and the shape of a beam emitted from the probe 106. The processors 116 also are in electronic communication with a display device 118, and the processors 116 may process the data into images for display on the display device 118. The processors 116 may include one or more central processors (CPU) according to an embodiment. According to other embodiments, the processors 116 may include one or more other electronic components capable of carrying out processing functions, such as one or more digital signal processors, field-programmable gate arrays (FPGA), graphic boards, and/or integrated circuits. According to other embodiments, the processors 116 may include multiple electronic components capable of carrying out processing functions. For example, the processors 116 may include two or more electronic components selected from a list of electronic components including: one or more central processors, one or more digital signal processors, one or more field-programmable gate arrays, and/or one or more graphic boards. According to another embodiment, the processors 116 may also include a complex demodulator (not shown) that demodulates the radio frequency data and generates raw data. In another embodiment, the demodulation can be carried out earlier in the processing chain.

The processors 116 are adapted to perform one or more processing operations according to a plurality of selectable ultrasound modalities on the data. The data may be processed in real-time during a scanning session as the echo signals are received, such as by processing the data without any intentional delay or processing the data while additional data is being acquired during the same imaging session of the same patient. For example, an embodiment may acquire images at a real-time rate of seven to twenty volumes per second. The real-time volume-rate may be dependent on the length of time needed to acquire each volume of data for display, however. Accordingly, when acquiring a relatively large volume of data, the real-time volume-rate may be slower. Some embodiments may have real-time volume-rates that are considerably faster than twenty volumes per second while other embodiments may have real-time volume-rates slower than seven volumes per second.

The data may be stored temporarily in a buffer (not shown) during a scanning session and processed in less than real-time in a live or off-line operation. Some embodiments of the inventive subject matter may include multiple processors (not shown) to handle the processing tasks that are handled by the processors 116 according to the exemplary embodiment described hereinabove. For example, a first processor may be utilized to demodulate and decimate the RF signal while a second processor may be used to further process the data prior to displaying an image. It should be appreciated that other embodiments may use a different arrangement of processors.

The ultrasound imaging system 100 may continuously acquire data at a volume-rate of, for example, ten to thirty hertz. Images generated from the data may be refreshed at a similar frame-rate. Other embodiments may acquire and display data at different rates. For example, some embodiments may acquire data at a volume-rate of less than ten hertz or greater than thirty hertz depending on the size of the volume and the intended application.

A memory 120 is included for storing processed volumes of acquired data. In one embodiment, the memory 120 is of sufficient capacity to store at least several seconds worth of volumes of ultrasound data. The volumes of data are stored in a manner to facilitate retrieval thereof according to its order or time of acquisition. The memory 120 may comprise any known data storage medium, such as one or more tangible and non-transitory computer-readable storage media (e.g., one or more computer hard drives, disk drives, universal serial bus drives, or the like).

Optionally, one or more embodiments of the inventive subject matter described herein may be implemented utilizing contrast agents. Contrast imaging generates enhanced images of anatomical structures and blood flow in a body when using ultrasound contrast agents including microbubbles. After acquiring data while using a contrast agent, the image analysis includes separating harmonic and linear components, enhancing the harmonic component and generating an ultrasound image by utilizing the enhanced harmonic component. Separation of harmonic components from the received signals is performed using suitable filters.

In various embodiments of the present invention, data may be processed by other or different mode-related modules by the processors 116 (e.g., B-mode, Color Doppler, M-mode, Color M-mode, spectral Doppler, Elastography, TVI, strain, strain rate, and the like) to form two- or three-dimensional image data. For example, one or more modules may generate B-mode, color Doppler, M-mode, color M-mode, spectral Doppler, Elastography, TVI, strain, strain rate and combinations thereof, and the like. The image beams and/or volumes are stored and timing information indicating a time at which the data was acquired in memory may be recorded. The modules may include, for example, a scan conversion module to perform scan conversion operations to convert the image volumes from beam space coordinates to display space coordinates. A video processor module may read the image volumes from a memory and displays an image in real time while a procedure is being carried out on a patient. A video processor module may store the images in an image memory, from which the images are read and displayed.

Figure 2:
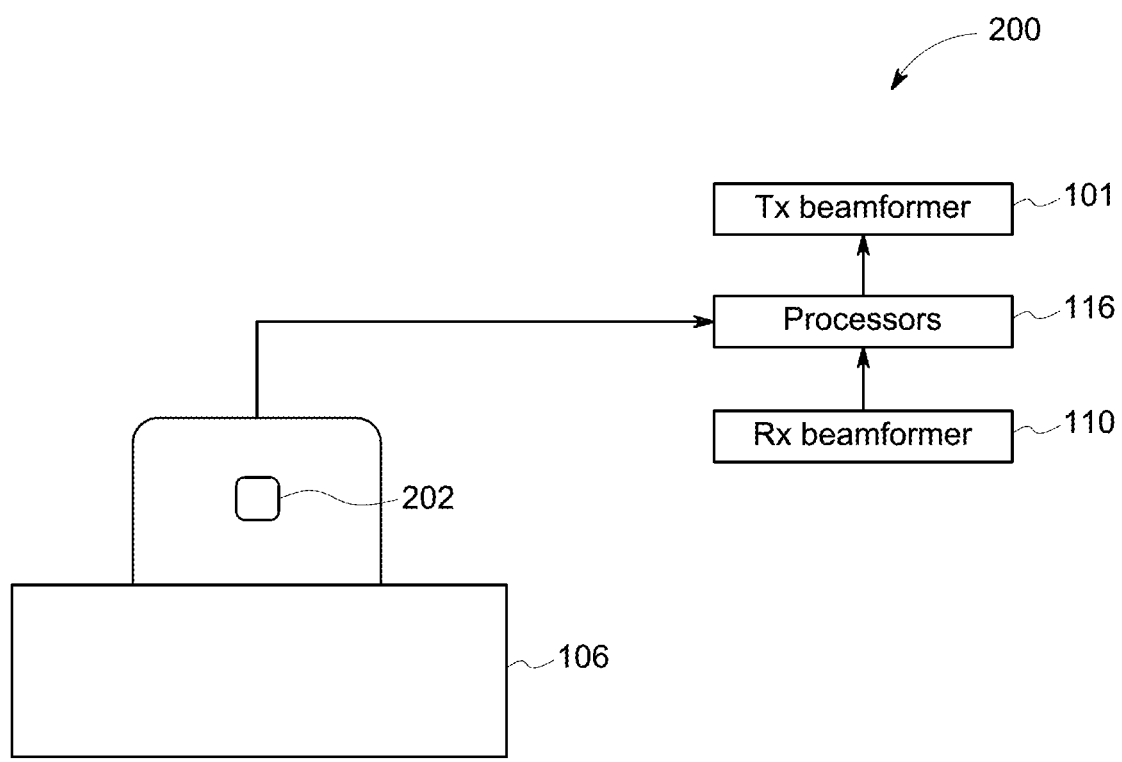
FIG. 2 schematically illustrates one embodiment of a control apparatus of the imaging system shown in FIG. 1.

FIG. 2 schematically illustrates one embodiment of a control apparatus 200 of the imaging system 100. Although not shown in FIG. 1, the control apparatus 200 can be included in the imaging system 100. For example, the control apparatus 200 can include the processors 116 and optionally can include one or more of the transmit beamformer 101 and/or the receive beamformer 110. Optionally, the processors that implement the operations performed by the control apparatus 200 may be additional or other processors than those shown in FIG. 1. For example, the operations performed by the processors 116 in connection with the imaging system 100 described in connection with FIG. 1 may not be performed by the same processor(s) that perform the operations of the control apparatus 200.

The control apparatus 200 includes or communicates with one or more movement sensors 202 that are operatively coupled with the probe 106. For example, the processors 116 can communicate with one or more accelerometers in and/or on the probe 106 to receive motion data from the accelerometers to monitor the motion of the probe 106. Additionally or alternatively, the movement sensors 202 can be external or separate from the probe 106, such as a radar system, LiDAR system, camera system, or the like, that generate data indicative of the movement (or lack thereof) of the probe 106. The processors 116 and sensors 202 can be coupled by wired and/or wireless connections to communicate the data indicative of movement of the probe 106 while an operator is using the probe 106 to obtain image data of a region of interest in one or more imaged bodies.

The processors 116 monitor motion of the imaging probe 106 in the imaging system 100 to control a time-varying parameter of the imaging system 100. The value of the parameter can be changed based on the motion of the imaging probe 106 that is monitored. The processors 116 can change the time-varying parameter of the imaging system 100 based on the motion of the imaging probe 106 to change image data that is acquired of an imaged body by the imaging probe 106.

The processors 116 can examine accelerations or other movements of the probe 106 (as indicated by data from the sensors 202) to monitor motion of the imaging probe 106. This motion data can indicate to the processors 116 whether the probe 106 is stationary or moving, how long the probe 106 has been stationary or moving, the speed at which the probe 106 is moving, the direction(s) in which the probe 106 is moving, the orientation of the probe 106 (while moving or stationary), and/or other information about movement (or the lack thereof) of the probe 106.

Based on the movement data provided by the sensor(s) 202, the processors 116 can change a time-varying parameter of the imaging system 100. The parameter of the imaging system 100 can be time-varying in that the value of the parameter can be changed at different times or as a function of time based on the motion of the probe 106 being monitored. The value of a parameter of the imaging system 100 can continue to change at the same rate, at a rate that increases or accelerates with respect to time, and/or a rate that decreases or decelerates with respect to time based on the motion of the probe 106. In one embodiment, the parameter of the imaging system 100 can have a first value while the operator is moving the imaging probe 106. Responsive to the operator holding the imaging probe 106 still for at least a designated period of time (e.g., five seconds or more), the processors 116 can begin to change the value of the parameter from the first value, such as by increasing the gain, increasing the number of scan lines, increasing the refresh rate, or the like. Responsive to the operator moving the imaging probe 106 again, the value of the parameter may return to the first value. Alternatively, the parameter value may change to another default value.

For example, a gain at which the probe 106 (or processors 116) amplify received echoes of ultrasound pulses can be set (by default, by an operator of the probe 106, and/or automatically by the processors 116) to have a first value while the operator is using the probe 106 to obtain image data of a region of interest in a body. The body can be a human patient, an anatomy of the patient, or a non-human object, such as a machine or component under examination. The operator may move the probe 106 and examine the image data presented on the display device 118 (shown in FIG. 1). The operator can stop moving the probe 106 once the field of view of the probe 106 results in the image data revealing or capturing a volume or area of interest in the body (e.g., a region of interest in the body). Responsive to detecting the cessation of movement of the probe 106, the processors 116 can automatically, and without operator input or other intervention, increase the value of the gain of the imaging system 100. The operator can continue to view the image data that is output by the imaging system 100 on the display device 118 as the value of the gain continues to increase. The gain can be increased by a default amount and then stop increasing, can continue to increase until the operator begins moving the probe 106 again, can increase by a fixed, discrete amount (e.g., a step amount) and then hold at that value. The value of the gain can be held at this value for a default amount of time (e.g., five seconds or the like), or until the operator provides some input (e.g., audibly, via touch, and/or by moving the probe 106).

In one embodiment, the processors 116 do not change the value of the operational parameter of the imaging system 100 unless or until the probe 106 is held stationary for at least a designated period of time. For example, the processors 116 may require that the probe 106 be held still for a non-instantaneous period of time (e.g., at least two seconds, at least five seconds, or the like) to ensure that the operator is not merely resting or is wanting to briefly view a region of interest without changing the parameter based on the probe 106 being held stationary for a brief time.

The processors 116 can change the value of the operational parameter responsive to detecting movement of the probe 106. For example, in addition to or instead of changing the value of the parameter responsive to the probe 106 being held stationary, the processors 116 can examine data from the sensors 202 to determine whether the probe 106 is moving. Responsive to determining that the probe 106 is moving, the processors 116 can change the value of the parameter of the imaging system.

The processors 116 can require that the probe 106 move in a designated way before changing the value of the operational parameter to ensure that the detected movement is indicative of the operator wanting to change the operational parameter. For example, the processors 116 can examine the data from the sensors 202 to determine how rapidly the probe 106 is moving and, responsive to the probe 106 moving faster than a designated, non-zero velocity or rate, the processors 116 change the value of the imaging parameter. If the probe 106 is moving, but moving slower than the designated rate, then the processors 116 may not automatically change the value of the parameter.

Optionally, the processors 116 can examine the motion of the probe 106, determine that the probe 106 is moving slowly, but still change the value of the imaging parameter. For example, the operator may attempt to hold the probe 106 stationary, but may slightly move the probe 106 unintentionally. The processors 116 can monitor the motion of the probe 106 based on the data from the sensors 202 and determine that the probe 106 is moving, but is not moving rapidly enough and/or by a great enough of a distance to indicate that the operator does not want to change the imaging parameter. As a result, the processors 116 can change the value of the parameter.

The processors 116 can associate different types or categories of motion of the probe 106 with different imaging parameters and/or different changes to the imaging parameters. For example, the probe 106 may be actuated by the operator in a sequence of different movements. This sequence can be associated with an imaging parameter of the imaging system 100 and/or a change to an imaging parameter. Different sequences of motion of the probe 106 can be associated with different imaging parameters and/or different changes to an imaging parameter. The processors 116 can examine the data from the sensors 202 to determine a sequence of motion (e.g., movements and/or holding stationary) of the probe 106. Different designated sequences of probe motion can be stored in the memory 120 (shown in FIG. 1) and associated with different imaging parameters and/or different changes to an imaging parameter. The processors 116 can access these designated sequences and compare the motion sequence represented by the sensor data (e.g., the detected motion sequence) with the designated motion sequences. If the detected motion sequence matches or more closely matches one designated motion sequence (e.g., matches exactly or more closely matches relative to one or more, or all, other designated motion sequences), then the processors 116 can determine which imaging parameter is to be changed and/or how the parameter is to be changed from the memory 120. The processors 116 can then implement this change.

The sequences of probe motion can include a variety of motions. For example, holding the probe stationary for a designated period of time (e.g., two seconds) can be a first motion in a first sequence and then rotating the probe 106 in a clockwise direction can be a second motion in the first sequence. Responsive to determining that the probe 106 has been moved according to this first sequence, the processors 116 can determine which parameter is to be changed (e.g., the two-dimensional line density) and/or how much to change the value of the parameter (e.g., increase the parameter by 10%). As another example, holding the probe stationary for the designated period of time can be a first motion in a different, second sequence and then rotating the probe 106 in a counter-clockwise direction can be a second motion in the second sequence. Responsive to determining that the probe 106 has been moved according to this second sequence, the processors 116 can determine which parameter is to be changed (e.g., the receive frequency) and/or how much to change the value of the parameter (e.g., decrease the parameter by 8%). These sequences are provided merely as examples, and are not limiting on all embodiments of the inventive subject matter. For example, some sequences may not involve holding the probe 106 stationary and/or rotating the probe 106.

The different designated motion sequences can represent different types or categories of motion. Optionally, a sequence can be a single motion of the probe 106. For example, holding the probe 106 stationary can be a single movement of a first designated sequence that dictates how an imaging parameter is to be changed and/or how the value of the parameter is to be changed.

In one embodiment, the parameter that is changed based on detected motion of the probe 106 is the starting and/or stopping of recording of a video. The operator can move (or not move) the probe 106 in a way that is associated (in the memory 120) with starting the recording of a video, such as a cine start operation. The processors 116 can begin saving a moving video of the image data from the probe 106 (e.g., in the memory 120) and/or present this video on the display device 118. Responsive to detecting the same or other motion of the probe 106, the processors 116 can stop recording of the video, or implement a cine stop operation.

The parameter that is changed based on detected motion of the probe 106 can be an acquisition of a still image or photo. The operator can move (or not move) the probe 106 in a way that is associated with the capture of a still photo. The processors 116 can then save a static image from the image data from the probe 106 and/or present this video on the display device 118.

The imaging system 100 described herein can allow for an operator of the probe 106 to set and/or change imaging parameters without having to provide any other input aside from moving (or not moving) the probe 106. The imaging system 100 can change imaging parameters based on monitored motion of the probe 106 without the operator having to actuate any input devices (other than the probe 106), without the operator having to speak for voice-activated control or to instruct another operator to change a parameter, or the like.

In one embodiment, the processors 116 measure an image quality of the image data acquired or generated using the probe 106, and determine whether to change an imaging parameter based on the image quality. The image quality can be a quantity that represents how clearly the image data shows a region of interest in a body under examination. Images that more clearly indicate or depict the region of interest can be associated with a higher value for the image quality, while images that do not as clearly indicate or depict the region of interest can be associated with a lower value for the image quality. The processors 116 can determine the image quality by monitoring motion of the probe 106. Different types and/or amounts of movement of the probe 106 can be associated with different values of image quality. For example, a probe 106 that is held stationary for a period of time can have a large value for the image quality, while a probe 106 held stationary for a shorter period of time can have a smaller value of the image quality, while a probe 106 being slowly moved can have an even smaller value of the image quality, while a probe 106 being more rapidly moved can have an even smaller value of the image quality.

The processors 116 can monitor motion of the probe 106, calculate an image quality value of the image data coming from the probe 106, and optionally change an imaging parameter based on the value of the image quality. For example, if the image quality falls below a designated threshold associated with poor image quality, then the processors 116 can change the parameter. The value of this threshold can represent or indicate an amount of motion artifacts in the image data. Larger thresholds can indicate more motion artifacts appearing in the image data, while smaller thresholds can indicate fewer motion artifacts in the image data.

The operator may be moving the probe 106 around to find the region of interest in a body. The sensitivity, gain, line density, and the like, of the imaging system 100 may be decreased in value by the processors 116 while the operator is moving the probe 106 around so that the image data is not too sensitive or contain too much information to be intelligible to the operator. Responsive to the movement of the probe slowing or stopping, the processors 116 can increase the sensitivity, gain, line density, or the like, due to an increase in the image quality due to the slowing or stopping of the probe 106.

During an imaging session, the operator can continue moving or not moving the probe 106, and the processors 116 can repeatedly monitor the motion of the probe 106 to determine whether and/or how to change parameters of the imaging system 100. This can assist the operator in dedicating more attention toward the placement of the probe 106 and the resulting image data than current systems which can at least partially distract the operator with having to both manipulate the probe 106 and also manually change the imaging parameters by inputting the changes into a keyboard, touchscreen, etc.

Figure 3:
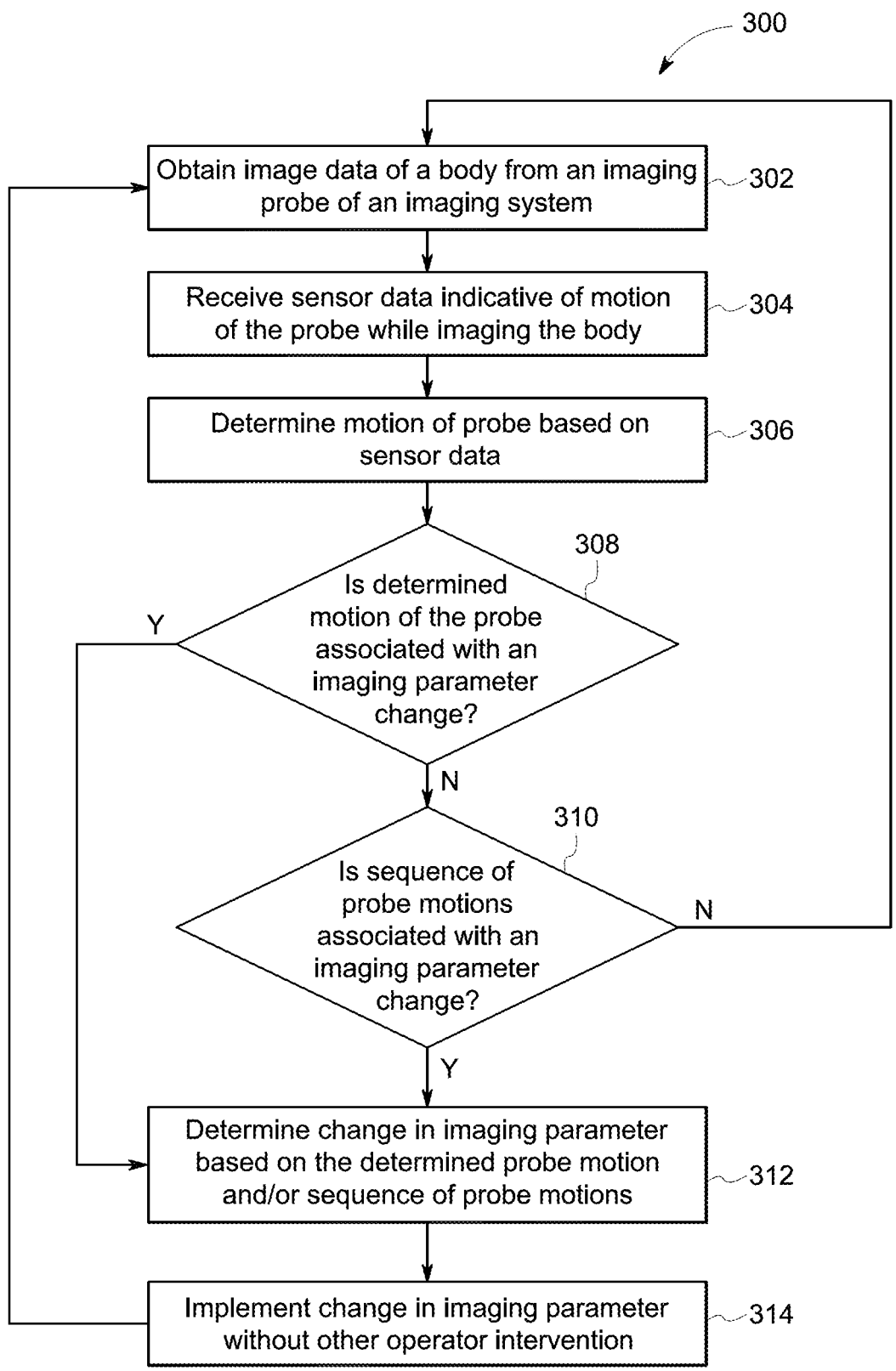
FIG. 3 illustrates a flowchart of one embodiment of a method for automatically modifying parameters of an imaging system.

FIG. 3 illustrates a flowchart of one embodiment of a method 300 for automatically modifying parameters of an imaging system. The method 300 can represent operations performed by the processors 116 (shown in FIG. 1) during an imaging session where an operator is manually actuating the imaging probe 106 (shown in FIG. 1) to obtain image data representative of a region of interest within a body. In one embodiment, the memory 120 stores instructions that, when implemented by the processors 116, direct the operations of method 300 (and/or other operations described herein) to be performed by the processors 116.

Performance of the method 300 can allow for an operator to continue imaging the region of interest while concurrently modifying the parameters that dictate how the image data is obtained and/or generated, without providing other intervention or action with the imaging system 100 (shown in FIG. 1). This can reduce the operator-interface requirements of the imaging system 100 so that the imaging system 100 is able to customize or tailor the parameters used to create the imaging system 100 without requiring additional input aside from movement of the probe 106.

At 302, image data of a body is obtained using an imaging probe of an imaging system. For example, the probe 106 can be used to obtain image data representative of a field of view or region of interest of a body. At 304, sensor data indicative of motion of the imaging probe is received while the body is being imaged. The sensor data can be provided from motion sensors, such as accelerometers, that are coupled with the probe 106. The data can indicate motion of the probe 106, such as whether the probe 106 is moving, how the probe 106 is moving, the direction(s) in which the probe 106 is moving, the speed at which the probe 106 is moving, or the like. This data can be provided to the processors 116, as described above.

At 306, motion of the probe is determined based on the sensor data. For example, the processors 116 can receive the data from accelerometers or other sensors that indicate how and/or whether the probe 106 is being moved. The processors 116 can examine this data to monitor how the probe 106 is moving and/or whether the probe 106 is held stationary. For example, accelerations in different directions can indicate where and/or how fast the probe 106 is being moved.

At 308, a determination is made as to whether the motion of the probe is associated with a change in an imaging parameter. The processors 116 can examine the motion of the probe 106 and determine if the motion is associated with an imaging parameter and/or an amount of change in the parameter. As described above, holding the probe 106 stationary, moving the probe 106, moving the probe 106 slower than a designated threshold, moving the probe 106 faster than the same or another threshold, and/or moving the probe 106 in a designated direction (or along a designated vector) can be associated with a parameter of the imaging system 100 and/or a change to the imaging parameter. If the motion of the probe 106 is associated with a parameter or parameter change, then flow of the method 300 can proceed toward 312. If the motion of the probe 106 is not associated with the parameter or parameter change, then flow of the method 300 can proceed toward 310. For example, the single movement or combination of two or more movements alone may not be associated with any parameter or parameter change.

At 310, a determination is made as to whether a sequence of motions of the probe is associated with a change in an imaging parameter. While a single or combination of motions of the probe 106 may not be associated with an imaging parameter or parameter change by the processors 116, a longer series of sequential movements of the probe 106 may be associated with the parameter or parameter change. Different motion sequences can be associated with different parameters or parameter changes. If the processors 116 determine that a sequence of detected motions of the probe 106 is associated with a parameter or parameter change, then flow of the method 300 can proceed toward 312. Otherwise, the monitored motion of the probe 106 is not identified by the processors 116 with any parameter or change in parameter. As a result, flow of the method 300 can return toward 302. This can allow for the imaging session to continue without changing the parameter using motion of the probe 106. Optionally, flow of the method 300 can terminate.

At 312, a change in an imaging parameter is determined. The processors 116 can refer to the memory 120 shown in FIG. 1 (or another location) to determine what parameter and/or parameter change is associated with the identified probe motion (e.g., from 306 and 308) and/or sequence of probe motions (e.g., from 306 and 310). Some different probe motions and/or motion sequences can be associated with different parameters and/or parameter changes in the memory 120 (or elsewhere), and the processors 116 can access this information to determine which parameter to change and/or how to change the parameter.

At 314, the imaging parameter change is implemented. The processors 116 can automatically change the imaging parameter, without operator intervention other than movement or holding of the probe. This can reduce the amount and/or source of input information needed by the imaging system 100 to change the image data being obtained by the probe 106, as described above.

Figure 4:
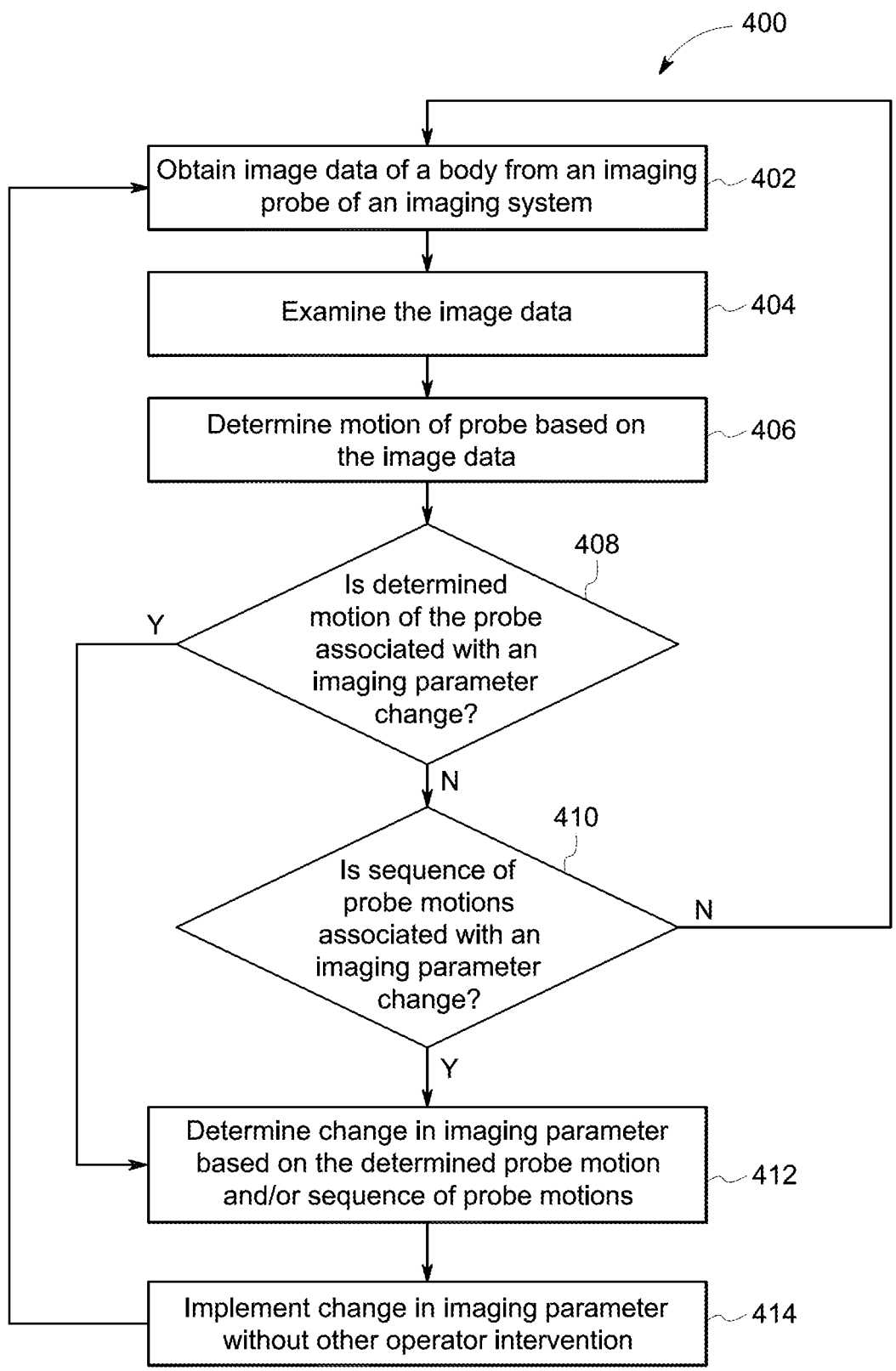
FIG. 4 illustrates a flowchart of another embodiment of a method for automatically modifying parameters of an imaging system.

FIG. 4 illustrates a flowchart of another embodiment of a method 400 for automatically modifying parameters of an imaging system. The method 400 can represent operations performed by the processors 116 (shown in FIG. 1) during an imaging session where an operator is manually actuating the imaging probe 106 (shown in FIG. 1) to obtain image data representative of a region of interest within a body. In one embodiment, the memory 120 stores instructions that, when implemented by the processors 116, direct the operations of method 300 (and/or other operations described herein) to be performed by the processors 116.

Similar to the method 300, performance of the method 400 can allow for an operator to continue imaging the region of interest while concurrently modifying the parameters that dictate how the image data is obtained and/or generated, without providing other intervention or action with the imaging system 100 (shown in FIG. 1). This can reduce the operator-interface requirements of the imaging system 100 so that the imaging system 100 is able to customize or tailor the parameters used to create the imaging system 100 without requiring additional input aside from movement of the probe 106. One difference between the flowcharts of the methods 300, 400 shown in FIGS. 3 and 4 is the reliance on sensors 202 to detect motion of the probe 106. The method 300 includes determining motion of the probe 106 based on output from the sensor 202 (e.g., at 306), while the method 400 does not necessarily require or rely on sensor output. As described below, the method 400 involves examining image data to identify motion of the probe 106, which can then be used to change one or more parameters of the imaging system 100.

At 402, image data of a body is obtained using an imaging probe of an imaging system. For example, the probe 106 can be used to obtain image data representative of a field of view or region of interest of a body. At 404, the image data that is acquired using the imaging probe is examined. The image data can be examined to determine whether the image data indicates that the probe is moving. For example, one or more cross-correlation techniques, speckle tracking, optical flow analysis, or the like, can be used to examine the image data to determine whether the image data changes with respect to time and how the image data changes with respect to time. In one embodiment, different frames of the image data (indicative of the image data acquired at different times) can be examined and compared with each other to identify differences in the image data.

At 406, motion of the probe is determined based on the image data. For example, the processors 116 can receive the image data, identify differences or changes in the image data with respect to time (e.g., at 404), and identify movement of the probe 106 based on these differences. For example, imaging the same body with while the probe 106 is moving can result in different frames of the image data being different. The body or one or more parts of the body may be in different locations in the image frames if the probe 106 is moving. The change in locations or other differences in the image data can reveal how the probe 106 is moving, such as which direction the probe 106 is moving and/or how rapidly the probe 106 is moving. This probe motion can be identified without use of or reliance on output from a motion sensor, such as an accelerometer. This analysis of the image data to identify probe motion can occur while additional image data is being acquired. For example, during a continuous imaging session where the imaging probe 106 is acquiring image data of the body, frames of the image data can be examined to identify probe motion while additional frames are being obtained.

At 408, a determination is made as to whether the motion of the probe is associated with a change in an imaging parameter. The processors 116 can examine the motion of the probe 106 and determine if the motion is associated with an imaging parameter and/or an amount of change in the parameter. As described above, holding the probe 106 stationary, moving the probe 106, moving the probe 106 slower than a designated threshold, moving the probe 106 faster than the same or another threshold, and/or moving the probe 106 in a designated direction (or along a designated vector) can be associated with a parameter of the imaging system 100 and/or a change to the imaging parameter. If the motion of the probe 106 is associated with a parameter or parameter change, then flow of the method 400 can proceed toward 412. If the motion of the probe 106 is not associated with the parameter or parameter change, then flow of the method 400 can proceed toward 410. For example, the single movement or combination of two or more movements alone may not be associated with any parameter or parameter change.

At 410, a determination is made as to whether a sequence of motions of the probe is associated with a change in an imaging parameter. While a single or combination of motions of the probe 106 may not be associated with an imaging parameter or parameter change by the processors 116, a longer series of sequential movements of the probe 106 may be associated with the parameter or parameter change. Different motion sequences can be associated with different parameters or parameter changes. If the processors 116 determine that a sequence of detected motions of the probe 106 is associated with a parameter or parameter change, then flow of the method 400 can proceed toward 412. Otherwise, the monitored motion of the probe 106 is not identified by the processors 116 with any parameter or change in parameter. As a result, flow of the method 400 can return toward 402. This can allow for the imaging session to continue without changing the parameter using motion of the probe 106. Optionally, flow of the method 400 can terminate.

At 412, a change in an imaging parameter is determined. The processors 116 can refer to the memory 120 shown in FIG. 1 (or another location) to determine what parameter and/or parameter change is associated with the identified probe motion (e.g., from 406 and 408) and/or sequence of probe motions (e.g., from 406 and 310). Some different probe motions and/or motion sequences can be associated with different parameters and/or parameter changes in the memory 120 (or elsewhere), and the processors 116 can access this information to determine which parameter to change and/or how to change the parameter.

At 414, the imaging parameter change is implemented. The processors 116 can automatically change the imaging parameter, without operator intervention other than movement or holding of the probe. This can reduce the amount and/or source of input information needed by the imaging system 100 to change the image data being obtained by the probe 106, as described above.

In yet another embodiment, the imaging system 100 and/or methods 300, 400 may identify motion of the probe 106 using a combination of data from the sensor 202 and analysis of imaging data. For example, another method of the inventive subject matter described herein can include a combination of the operations described in connection with 304, 306 in the method 300 and in connection with 404, 406 in the method 400. Such a combined or hybrid method can involve examining both the sensor data indicative of motion of the probe 106 and analysis of the image data to identify motion of the probe 106. In one embodiment, if at least one of the sensor data or the image data differences indicate probe motion, then this probe motion can be identified and used to change an imaging parameter, as described above. Otherwise, the imaging parameter is not automatically changed based on probe motion. In another embodiment, if both the sensor data and the image data indicate probe motion, then the imaging parameter is changed accordingly, as described above. Otherwise, the imaging parameter is not automatically changed based on probe motion.

In one embodiment, an apparatus includes one or more processors configured to monitor motion of an imaging probe in an imaging system operating according to one or more parameters. The imaging probe is configured to output image data representative of an imaged body. The one or more processors are configured to change the one or more parameters of the imaging system based on the motion of the imaging probe that is monitored.

Optionally, the one or more processors are configured to be communicatively coupled with one or more motion sensors operably coupled with the imaging probe. The one or more processors are configured to identify the motion of the imaging probe based on motion data that is output by the one or more motion sensors.

Optionally, the one or more processors are configured to monitor the motion of the imaging probe by examining the image data and identifying the motion of the imaging probe based on the image data.

Optionally, the one or more processors are configured to monitor the motion of the imaging probe by determining that the imaging probe is stationary. The one or more processors can be configured to change the one or more parameters of the imaging system responsive to determining that the imaging probe is held stationary.

Optionally, the one or more processors are configured to change a value of the one or more parameters with respect to time while the imaging probe is held stationary.

Optionally, the one or more processors are configured to change the one or more parameters of the imaging system such that the imaging probe acquires the image data at a different sensitivity responsive to a change in the motion of the imaging probe.

Optionally, the one or more processors are configured to change the one or more parameters of the imaging system such that the imaging probe one or more of starts or stops acquiring the image data responsive to a change in the motion of the imaging probe.

Optionally, the one or more processors are configured to direct the imaging probe to acquire a stationary image of the imaged body based on the motion of the imaging probe that is monitored.

Optionally, the one or more processors are configured to change the one or more parameters of the imaging system by changing one or more of a gain, a time gain compensation, a line density, a receipt frequency, a speckle reduction filter setting, a refresh rate, or a render setting of the imaging system.

Optionally, the one or more processors are configured to change the one or more parameters of the imaging system based on the motion of the imaging probe and without receiving or determining any other manual input provided by an operator of the imaging system or the imaging probe.

Optionally, the one or more processors are configured to calculate an image quality measure based on the motion of the imaging probe that is monitored. The one or more processors can be configured to change the one or more parameters of the imaging system responsive to the image quality measure exceeding or falling below a designated threshold.

In one embodiment, a method includes obtaining image data of an imaged body using a moveable imaging probe of an imaging system that operates according to one or more parameters, monitoring motion of the imaging probe while the imaging probe is obtaining the image data of the imaged body, and changing the one or more parameters of the imaging system using one or more processors based on the motion of the imaging probe that is monitored.

Optionally, the motion of the imaging probe is monitored based on data output by one or more sensors operatively coupled with the imaging probe.

Optionally, the motion of the imaging probe is monitored based on analysis of the image data.

Optionally, monitoring the motion of the imaging probe includes determining that the imaging probe is held stationary. The one or more parameters of the imaging system can be changed responsive to determining that the imaging probe is held stationary.

Optionally, a value of the one or more parameters are changed with respect to time while the imaging probe is held stationary.

In one embodiment, a tangible and non-transitory computer-readable storage medium is provided that includes instructions that direct one or more processors to monitor motion of an imaging probe of an imaging system that operates according to one or more parameters. The motion of the imaging probe is monitored while the imaging probe is obtaining the image data of an imaged body. The motion of the imaging probe is monitored based on one or more of data output by one or more sensors operatively coupled with the imaging probe or based on one or more changes in the image data. The instructions also direct the one or more processors to change the one or more parameters of the imaging system using one or more processors based on the one or more of the data output by the one or more sensors or based on the one or more changes in the image data.

Optionally, the instructions direct the one or more processors to monitor the motion of the imaging probe by determining that the imaging probe is held stationary and change the one or more parameters of the imaging system responsive to determining that the imaging probe is held stationary.

Optionally, the instructions direct the one or more processors to monitor the motion of the imaging probe by determining that the imaging probe is moving and change the one or more parameters of the imaging system responsive to determining that the imaging probe is moving.

Optionally, the instructions are configured to direct the one or more processors to change the one or more parameters of the imaging system by one or more of modifying a sensitivity at which the imaging probe acquires the image data, starting acquisition of the image data, stopping the acquisition of the image data, or changing one or more of a gain, a time gain compensation, a line density, a receipt frequency, a speckle reduction filter setting, a refresh rate, or a render setting of the imaging system.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements that do not have that property.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. An apparatus comprising:
   one or more processors configured to monitor motion of
      an imaging probe in an imaging system operating according to one or more time-varying parameters, the imaging probe configured to output image data representative of an imaged body, wherein the one or more processors are configured to change the one or more time-varying parameters of the imaging system over a time interval in which the imaging probe is held stationary based on the motion of the imaging probe that is monitored, wherein the one or more time-varying parameters are changed by different amounts based on how long the imaging probe is held stationary.

2. The apparatus of claim 1, wherein the one or more processors are configured to monitor the motion of the imaging probe by examining the image data and identifying the motion of the imaging probe based on the image data.

3. The apparatus of claim 1, wherein the one or more processors are configured to monitor the motion of the imaging probe by determining that the imaging probe is stationary, and the one or more processors are configured to change the one or more time-varying parameters of the imaging system by the different amounts in proportion to how long the imaging probe is held stationary.

4. The apparatus of claim 3, wherein the one or more time-varying parameters includes a sensitivity parameter, and the one or more processors are configured to increase the sensitivity parameter in proportion to how long the imaging probe is held stationary.

5. The apparatus of claim 1, wherein the one or more processors are configured to change the one or more time-varying parameters of the imaging system such that the imaging probe acquires the image data at different sensitivity values over the time interval in which the imaging probe is held stationary.

6. The apparatus of claim 1, wherein the one or more processors are configured to change the one or more time-varying parameters of the imaging system such that the imaging probe one or more of starts or stops acquiring the image data responsive to a change in the motion of the imaging probe.

7. The apparatus of claim 1, wherein the one or more processors are configured to direct the imaging probe to acquire a stationary image of the imaged body based on the motion of the imaging probe that is monitored.

8. The apparatus of claim 1, wherein the one or more processors are configured to change the one or more time-varying parameters of the imaging system by changing one or more of a gain, a time gain compensation, a line density, a receipt frequency, a speckle reduction filter setting, a refresh rate, or a render setting of the imaging system over the time interval in which the imaging probe is held stationary.

9. The apparatus of claim 1, wherein the one or more processors are configured to change the one or more time-varying parameters of the imaging system based on the motion of the imaging probe and without receiving or determining any other manual input provided by an operator of the imaging system or the imaging probe.

10. The apparatus of claim 1, wherein the one or more processors are configured to calculate an image quality measure based on the motion of the imaging probe that is monitored, the one or more processors configured to change the one or more time-varying parameters of the imaging system responsive to the image quality measure exceeding or falling below a designated threshold.

11. The apparatus of claim 1, wherein a value of the one or more time-varying parameters is changed at different times and/or as a function of time based on the motion of the imaging probe.

12. The apparatus of claim 1, wherein a value of the one or more time-varying parameters is changed at a same rate, at a rate that increases or accelerates with respect to time, and/or a rate that decreases or decelerates with respect to time based on the motion of the imaging probe.

13. The apparatus of claim 1, wherein responsive to the imaging probe being held stationary for at least a designated period of time of two seconds or more, the one or more processors begin to change the value of the one or more time-varying parameters over the different amounts in proportion to how long the imaging probe is held stationary.

14. The apparatus of claim 1, further comprising a display configured to display feedback showing at least one of a progress or current value of the one or more time-varying parameters.

15. A method comprising:
    obtaining image data of an imaged body using a moveable imaging probe of an imaging system that operates according to one or more time-varying parameters;
    monitoring motion of the imaging probe while the imaging probe is obtaining the image data of the imaged body; and
    changing the one or more time-varying parameters of the imaging system over a time interval in which the imaging probe is held stationary, using one or more processors, based on the motion of the imaging probe that is monitored, wherein the one or more time-varying parameters are changed by different amounts based on how long the imaging probe is held stationary.

16. The method of claim 15, wherein the motion of the imaging probe is monitored based on analysis of the image data.

17. The method of claim 15, wherein monitoring the motion of the imaging probe includes determining that the imaging probe is held stationary, wherein the one or more time-varying parameters of the imaging system is changed by the different amounts in proportion to how long the imaging probe is held stationary.

18. The method of claim 17, wherein a value of the one or more time-varying parameters includes a sensitivity parameter that is increased in proportion to how long the imaging probe is held stationary.

19. The method of claim 15, further comprising determining when the imaging probe has been held stationary for at least a designated period of time of two seconds or more and, in response thereto, beginning to change the value of the one or more time-varying parameters over the different amounts in proportion to how long the imaging probe is held stationary.

20. The method of claim 15, further comprising displaying feedback showing at least one of a progress or current value of the one or more time-varying parameters.

21. A tangible and non-transitory computer-readable storage medium comprising instructions that direct one or more processors to:
    monitor motion of an imaging probe of an imaging system that operates according to one or more time-varying parameters, the motion of the imaging probe monitored while the imaging probe is obtaining image data of an imaged body, the motion of the imaging probe monitored based on one or more changes in the image data; and change the one or more time-varying parameters of the imaging system over a time interval in which the imaging probe is held stationary, using one or more processors, based on the one or more changes in the image data, wherein the one or more time-varying parameters are changed by different amounts based on how long the imaging probe is held stationary.

22. The computer-readable storage medium of claim 21, wherein the instructions direct the one or more processors to:
   monitor the motion of the imaging probe by determining that the imaging probe is held stationary; and
   change the one or more time-varying parameters of the imaging system by the different amounts in proportion to how long the imaging probe is held stationary.

23. The computer-readable storage medium of claim 21, wherein the one or more time-varying parameters includes a sensitivity parameter, and wherein the instructions direct the one or more processors to:
   monitor the motion of the imaging probe by determining that the imaging probe is moving; and
   change the one or more time-varying parameters by decreasing the sensitivity parameter of the imaging system responsive to determining that the imaging probe is moving.

24. The computer-readable storage medium of claim 21, wherein the instructions are configured to direct the one or more processors to:
   change the one or more time-varying parameters of the imaging system by one or more of:
      modifying a sensitivity at which the imaging probe acquires the image data,
      starting acquisition of the image data,
      stopping the acquisition of the image data, or
      changing one or more of a gain, a time gain compensation, a line density, a receipt frequency, a speckle reduction filter setting, a refresh rate, or a render setting of the imaging system by the different amounts in proportion to how long the imaging probe is held stationary.

* * * * *